United States Patent [19]

Shoesmith

[11] Patent Number: Plant 5,282

[45] Date of Patent: Sep. 11, 1984

[54] CHRYSANTHEMUM PLANT NAMED CORONET

[75] Inventor: Leonard H. Shoesmith, Surrey, England

[73] Assignee: Pan American Plant Company, Parrish, Fla.

[21] Appl. No.: 405,920

[22] Filed: Aug. 6, 1982

[51] Int. Cl.[3] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Coronet and particularly characterized by its generally flat capitulum form, decorative capitulum type, yellow ray floret color, 40–90 mm. diameter across face of capitulum, approximately 300 mm. pot plant height measured from the top edge of the pot, semi-upright branching pattern, and by its 9 weeks response.

2 Drawing Figures

1

The present invention comprises a new and distinct cultivar of *Chrysanthemum morifolium,* Ramat., hereinafter referred to by the cultivar name Coronet.

Coronet is a product of a planned breeding program which had the objective of creating new chrysanthemum cultivars with decorative capitulum type, yellow ray floret color, 8–9 weeks flowering response, and having the ability to produce commercially acceptable quality in year round pot mum programs. Such traits in combination were not present in previously available commercial cultivars.

Coronet was originated from a hybridization made in a controlled breeding program in Westfield, Woking, England in 1976. The male and female parents are unknown at this time.

Coronet was discovered and selected as one flowering plant within the progeny of the parentage by Leonard H. Shoesmith in November, 1977 in a controlled environment in West Chicago, Ill., and given code number P7-442-Y. The first act of asexual reproduction of Coronet was accomplished when vegetative cuttings were taken from the initial selection in February, 1978 in a controlled environment in West Chicago, Ill. by a technician working under formulations established and supervised by Leonard H. Shoesmith. Horticultural examination of selected units initiated in March, 1978 has demonstrated that the combination of characteristics as herein disclosed for Coronet are firmly fixed and are retained through successive generations of asexual reproduction.

Coronet has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Coronet, which in combination distinguish this chrysanthemum as a new and distinct cultivar:

1. Generally flat capitulum form.
2. Decorative capitulum type.
3. Yellow ray floret color.

2

4. Diameter across the face of the capitulum 40–90 mm.
5. Medium pot plant height, approximately 300 mm. from top edge of the pot.
6. Semi-upright branching pattern.
7. 9 weeks response.

Of the many commercial cultivars known to the present inventor, the most similar in comparison to Coronet is Bright Golden Ann, an unpatented but commercial cultivar. In comparison to Bright Golden Ann, Coronet has a 7 to 10 days earlier response, is more compact and is generally smaller in the diameter of the capitulum. The ray floret color, capitulum form and capitulum type are similar to those same characteristics of Bright Golden Ann.

The accompanying photographic drawings show typical inflorescence and foliage characteristics of Coronet, with colors being as nearly true as possible with illustrations of this type. Sheet 1 is a color photograph in perspective of Coronet. Sheet 2 is a black and white photoprint of the underside of typical leaves of Coronet at various stages of growth or positioning on the plant.

In the following description color references are made to The Royal Horticultural Society Colour Chart. The color values were determined between 3:30–4:00 P.M. on May 24, 1982 under 3200K–500W intensity incandescent light at Bradenton, Fla.

CLASSIFICATION

Botanical: *Chrysanthemum morifolium,* Ramat., cv Coronet.

Commercial: Decorative pot mum.

INFLORESCENCE

Capitulum:

*Form.*—Generally flat.

*Type.*—Decorative.

*Diameter across face.*—40–90 mm.

Corolla of ray florets:

*Color (general tonality from a distance of three meters).*—Yellow (bright).

*Color (abaxial).*—7B.

*Color (adaxial).*—7A.

Corolla of disc florets:

*Mature.*—Fully double flower.

*Immature.*—Insignificant disc florets.

Reproductive organs:

*Androecium.*—In disc florets only.

*Gynoecium.*—In ray florets only.

PLANT

General appearance:

*Height.*—From top edge of pot approximately 300 mm.

Foliage:

*Color (abaxial).*—148A.

*Color (adaxial).*—147B.

*Shape.*—Deeply lobed and slightly serrated.

I claim:

1. A new and distinct cultivar of chrysanthemum cultivar named Coronet, as described and illustrated, and particularly characterized by its generally flat capitulum form, decorative capitulum type, yellow ray floret color, 40–90 mm. diameter across face of capitulum, approximately 300 mm. pot plant height measured from the top edge of the pot, semi-upright branching pattern, and by its 9 weeks response.

* * * * *

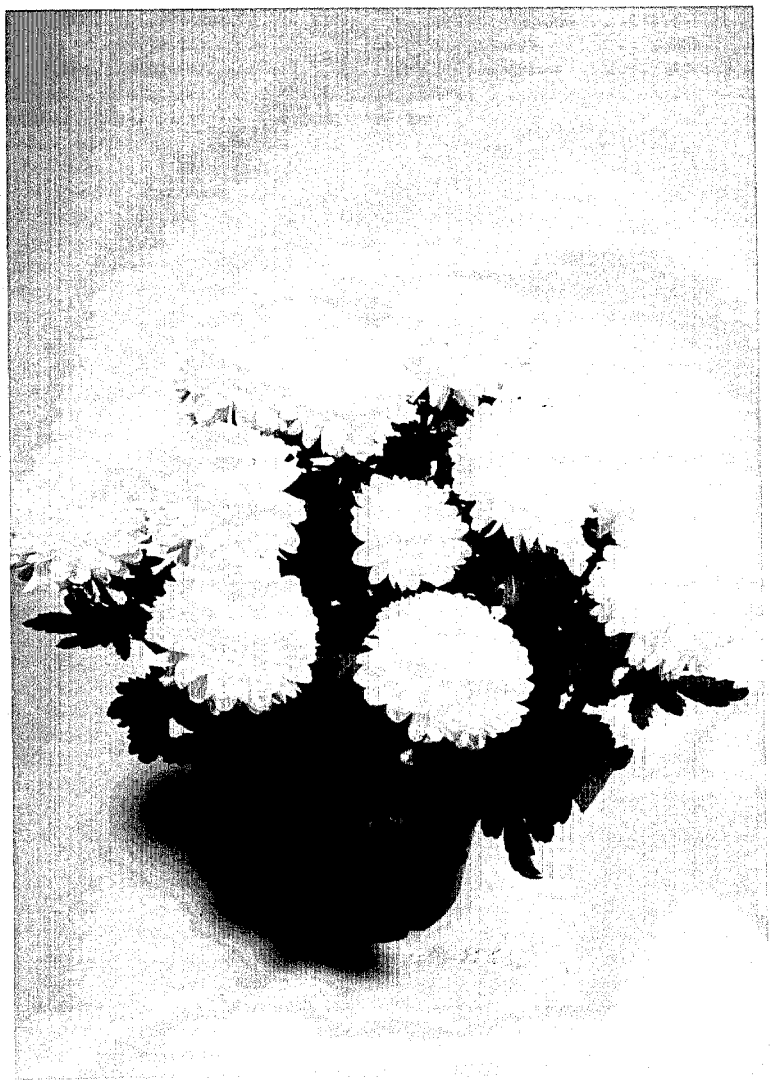

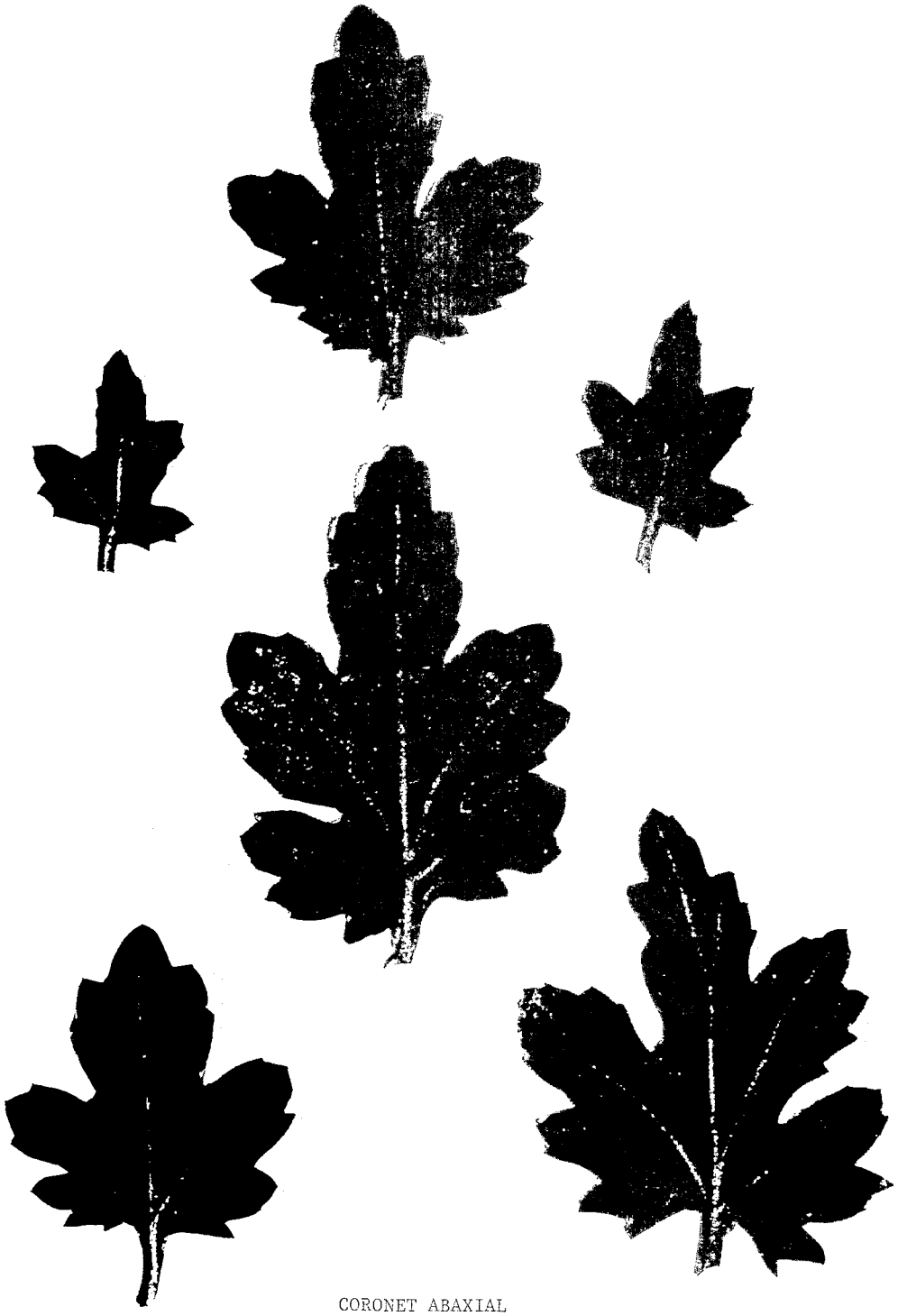
CORONET ABAXIAL